(12) United States Patent
Christman et al.

(10) Patent No.: US 9,011,348 B2
(45) Date of Patent: Apr. 21, 2015

(54) AIR SAMPLING APPARATUS AND METHODS

(75) Inventors: N. Thomas Christman, Greenfield, WI (US); Katherine M. Ross, West Allis, WI (US)

(73) Assignee: QuinTron Instrument Company, Inc., Milwaukee, WI (US)

( * ) Notice: Subject to any disclaimer, the term of this patent is extended or adjusted under 35 U.S.C. 154(b) by 983 days.

(21) Appl. No.: 12/456,814

(22) Filed: Jun. 23, 2009

(65) Prior Publication Data

US 2009/0318823 A1 Dec. 24, 2009

Related U.S. Application Data

(60) Provisional application No. 61/132,869, filed on Jun. 23, 2008.

(51) Int. Cl.
*A61B 5/08* (2006.01)
*A61B 5/097* (2006.01)
*G01N 1/24* (2006.01)

(52) U.S. Cl.
CPC ........ *A61B 5/097* (2013.01); *G01N 1/24* (2013.01); *G01N 2001/247* (2013.01); *G01N 2001/248* (2013.01)

(58) Field of Classification Search
CPC .............. G01N 2001/248; G01N 35/1016; A61B 5/082; A61B 5/097
USPC .................................. 600/529–543; 72/23.3
See application file for complete search history.

(56) References Cited

U.S. PATENT DOCUMENTS

| | | |
|---|---|---|
| 1,191,700 A | 7/1916 | Howes |
| 1,467,615 A | 9/1923 | Fairbanks |
| 2,795,223 A | 6/1957 | Stampe |
| 2,893,683 A | 7/1959 | Lane |
| 3,303,840 A | 2/1967 | Etzlinger |
| 3,388,705 A | 6/1968 | Grosshandler |
| 3,410,300 A | 11/1968 | Mondano |
| 3,426,745 A | 2/1969 | Farr |
| 3,544,273 A | 12/1970 | McConnaughey |
| 3,602,531 A | 8/1971 | Patry |
| 3,734,692 A | 5/1973 | Lucker et al. |
| 3,777,571 A | 12/1973 | Jaeger |

(Continued)

FOREIGN PATENT DOCUMENTS

| | | |
|---|---|---|
| DE | 4028387 | 3/1992 |
| FR | 1294835 | 4/1962 |

(Continued)

OTHER PUBLICATIONS

Rakow, N. A.; Suslick, K. S. "A Colorimetric Sensor Array for Odour Visualization" Nature, 2000, 406, 710-714.; Suslick, K. S.; Rakow, N. A. "Colorimetric Artificial Nose Having an Array of Dyes and Method for Artificial Olfaction".

*Primary Examiner* — Navin Natnithithadha
*Assistant Examiner* — Eric Messersmith
(74) *Attorney, Agent, or Firm* — Ryan Kromholz & Manion, S.C.

(57) ABSTRACT

An air sampling apparatus is disclosed, including a closed loop system for extracting air to be sampled into an analysis device such as a gas chromatograph, which is further coupled to an output. The closed loop sample extraction method reduces contaminants that can otherwise be introduced into air samples.

8 Claims, 5 Drawing Sheets

(56) References Cited

U.S. PATENT DOCUMENTS

| | | | |
|---|---|---|---|
| 3,817,108 A | 6/1974 | Principe et al. | |
| 3,858,573 A | 1/1975 | Ryan et al. | |
| 3,923,043 A | 12/1975 | Yanda | |
| 3,924,832 A | 12/1975 | Babcock | |
| 4,076,044 A | 2/1978 | Schindling | |
| 4,161,307 A | 7/1979 | Clinch et al. | |
| 4,327,741 A | 5/1982 | Watson et al. | |
| 4,470,412 A | 9/1984 | Nowacki et al. | |
| 4,506,665 A | 3/1985 | Andrews et al. | |
| 4,544,273 A | 10/1985 | Berndt | |
| 4,579,826 A | 4/1986 | Bolton et al. | |
| 4,580,556 A | 4/1986 | Kondur | |
| 4,585,254 A | 4/1986 | Adams | |
| 4,587,989 A | 5/1986 | Mayhew, Jr. | |
| 4,646,786 A | 3/1987 | Herder et al. | |
| 4,671,298 A * | 6/1987 | Babb et al. | 600/532 |
| 4,809,692 A | 3/1989 | Nowacki et al. | |
| 4,821,737 A | 4/1989 | Nelson | |
| 4,827,921 A | 5/1989 | Rugheimer | |
| 4,832,015 A | 5/1989 | Nowacki et al. | |
| 4,852,563 A | 8/1989 | Gross | |
| 4,852,583 A | 8/1989 | Walker | |
| 4,919,127 A | 4/1990 | Pell | |
| 4,938,210 A | 7/1990 | Shene | |
| 4,947,861 A | 8/1990 | Hamilton | |
| 4,953,547 A | 9/1990 | Poole, Jr. | |
| 5,012,803 A | 5/1991 | Foley et al. | |
| 5,012,804 A | 5/1991 | Foley et al. | |
| 5,042,500 A | 8/1991 | Norlien et al. | |
| 5,042,501 A | 8/1991 | Kenny et al. | |
| 5,062,423 A | 11/1991 | Matson et al. | |
| 5,066,597 A | 11/1991 | Stinson et al. | |
| 5,100,005 A | 3/1992 | Noble et al. | |
| 5,137,520 A | 8/1992 | Maxson et al. | |
| 5,140,993 A | 8/1992 | Opekun, Jr. et al. | |
| 5,165,393 A | 11/1992 | Kawaguchi | |
| 5,327,901 A | 7/1994 | Delente | |
| 5,346,089 A | 9/1994 | Brown et al. | |
| 5,432,094 A | 7/1995 | Delente | |
| 5,467,776 A * | 11/1995 | Hamilton | 600/543 |
| 5,573,005 A * | 11/1996 | Ueda et al. | 600/543 |
| 5,711,306 A | 1/1998 | Guilluy | |
| 5,834,626 A | 11/1998 | De Castro et al. | 73/23.3 |
| 5,957,839 A * | 9/1999 | Kruse et al. | 600/309 |
| 6,019,122 A | 2/2000 | Chen | |
| 6,368,558 B1 | 4/2002 | Suslick et al. | |
| 6,468,477 B1 * | 10/2002 | Hamilton et al. | 422/84 |
| 6,495,102 B1 | 12/2002 | Suslick et al. | |
| 6,541,272 B1 * | 4/2003 | Mitra | 436/178 |
| 6,712,770 B2 | 3/2004 | Lin et al. | 600/532 |
| 2004/0157281 A1 | 8/2004 | Hulkower et al. | |
| 2007/0066928 A1 * | 3/2007 | Lannoy | 604/6.07 |
| 2008/0041172 A1 * | 2/2008 | Jaffe et al. | 73/863.83 |
| 2008/0053439 A1 * | 3/2008 | Lighton | 128/204.22 |

FOREIGN PATENT DOCUMENTS

| | | |
|---|---|---|
| FR | 2497686 | 7/1982 |
| GB | 2230456 | 10/1990 |
| WO | 9311817 | 6/1993 |

\* cited by examiner

AIR SAMPLING APPARATUS AND METHODS

RELATED APPLICATION

This application claims the benefit of U.S. Provisional Patent Application Ser. No. 61/132,869, filed 23 Jun. 2008 and entitled "Air Sampling Apparatus and Methods."

BACKGROUND OF THE INVENTION

This invention relates to the field of sampling air from the lungs and specifically to the field of obtaining a sample of a person's air, including alveolar air from the alveoli of the lungs of a person.

Air from the lungs of a person can be used for many different types of testing that would otherwise require the person to undergo an invasive procedure. For example, alveolar air can be analyzed for, but not limited to, the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, necessary for specific testing. A peristaltic pump is a type of positive displacement pump used for pumping a variety of fluids. The fluid is contained within a flexible tube fitted inside a circular pump casing (though linear peristaltic pumps have been made). A rotor with a number of 'rollers', 'shoes' or 'wipers' attached to the external circumference compresses the flexible tube. As the rotor turns, the part of tube under compression closes (or 'occludes') thus forcing the fluid to be pumped to move through the tube. Additionally, as the tube opens to its natural state after the passing of the cam ('restitution') fluid flow is induced to the pump. This process is called peristalsis and is used in many biological systems such as the gastrointestinal tract.

Because the only part of the pump in contact with the fluid being pumped is the interior of the tube, it is easy to sterilize and clean the inside surfaces of the pump. Furthermore, since there are no moving parts in contact with the fluid, peristaltic pumps are inexpensive to manufacture. Their lack of valves, seals and glands makes them comparatively inexpensive to maintain, and the use of a hose or tube makes for a relatively low-cost maintenance item compared to other pump types.

A simple to use, inexpensive, and user-friendly apparatus is desired to collect and store human breath samples, and also to accurately extract samples from the storage.

The present invention is particularly suited for transferring air samples from a container to a gas or liquid analyzer. These samples are required to be kept at very pristine conditions, with no outside air influencing sample results.

SUMMARY OF THE INVENTION

The present invention incorporates is a closed system coupled to breath collection apparatus, such as a bag. One exemplary bag is described in commonly owned U.S. Pat. No. 6,468,477. In general, the invention involves capturing the air in a vacuum state, accessing the air sample by a hollow needle, and using a peristaltic pump to take the pressure down to atmospheric level, in a completely closed system to avoid introduction of waste air or contaminants into the sample.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
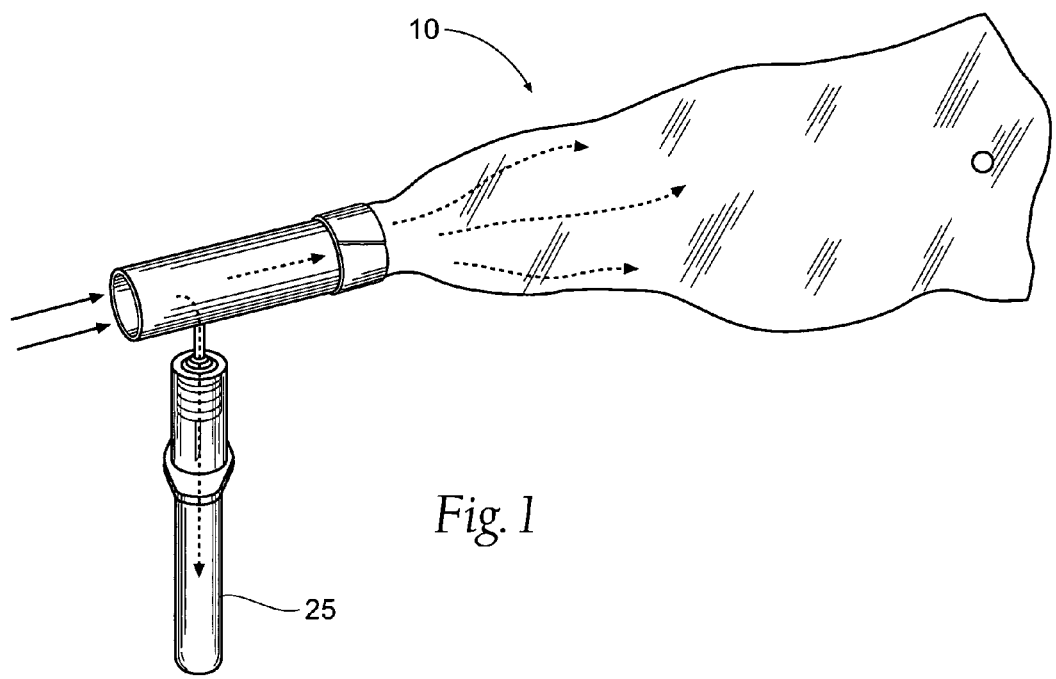
FIG. 1 is a side view of a breath collection bag of the present invention, coupled to a sensing mechanism for color analysis.
Figure 2:
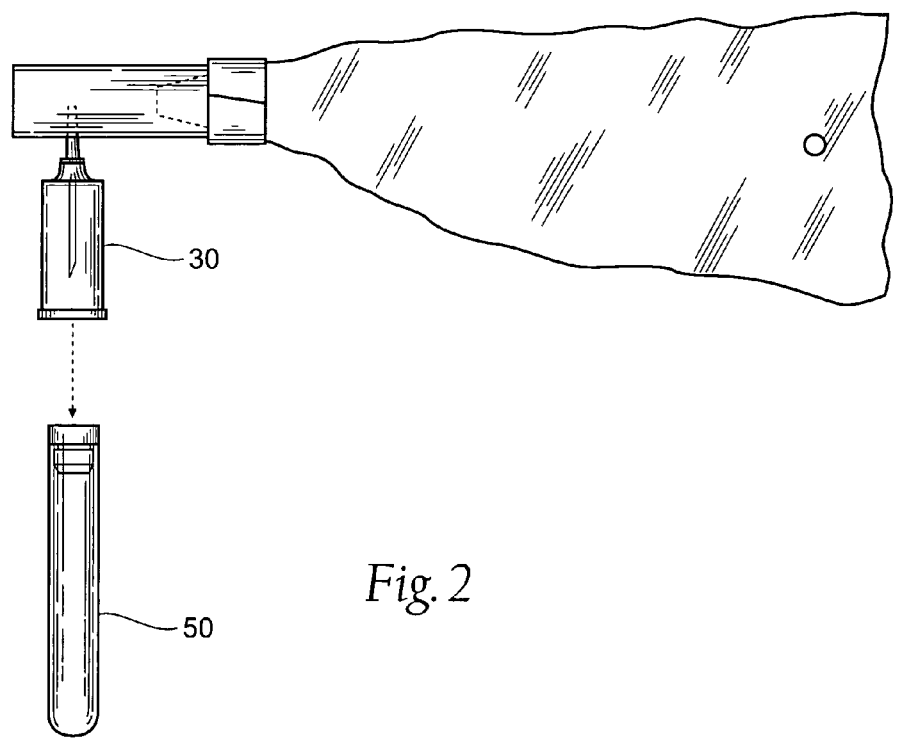
FIG. 2 is a side view of a bag and a breath intake structure, along with an evacuated tube being used for an air sampling collection apparatus.

Referring now to FIGS. 1 and 2, a side view of a breath collection bag of the present invention, coupled to a sample container. A breath intake structure is provided for a patient to breathe in, so that the breath can be captured by the breath collection bag. The breath sample, now consisting of preferably just alveolar air, is ready to be transferred into the test tube 50. It is noted that syringe 25 is initially empty, but is then filled by peristaltic pressure.

It is preferable, though not required, that the bag is of two ply construction, the two plies sealed together. Of course, more or less plies may be used in the bag construction. The bag structure is preferably expandable, and constructed of a supple, inert, and airtight material. One such supple and airtight material that performs suitably is thin polyester film, but foil laminate and a variety of other materials could also perform suitably. It should be easily recognizable to one skilled in the art that any number of materials other than foil laminate can be used for the bag structure 10. Other examples of materials that could be used for constructing the present invention include for illustration, but not by way of limitation: Tedlar®, Saranex®, Saran®, and Teflon®. Those skilled in the art will appreciate that the material can vary widely based on the characteristics of the gases desired to be sampled. The materials chosen should be inert and exhibit relative impermeability to the gases desired to sample, and any materials chosen that are relatively permeable to the gases desired to sample would not be preferred.

FIGS. 1 and 2 show that a tube, vial, bottle or bag sample container can be coupled to a device, including a syringe type device 25, for capturing breath.

Figure 3:
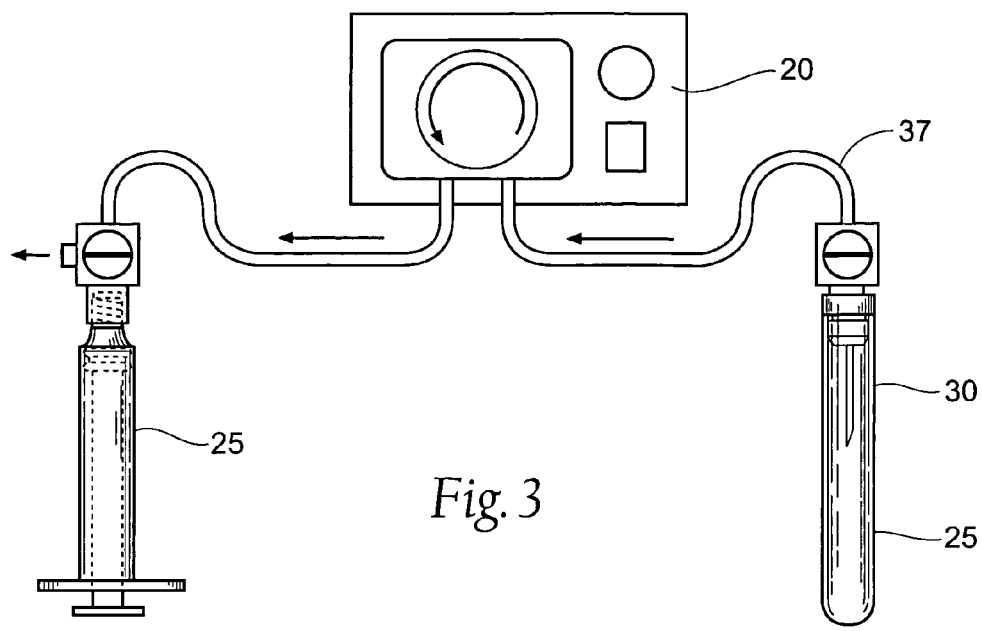
FIG. 3 is a side schematic view of an air sample extractor.
Figure 4:
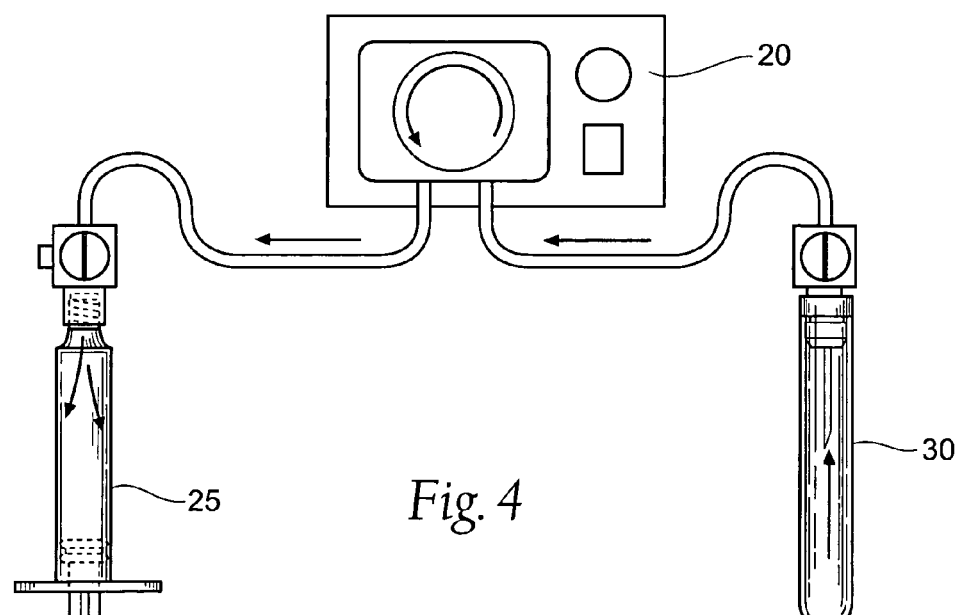
FIG. 4 is a side schematic view of an air sample extractor in use.
Figure 5:
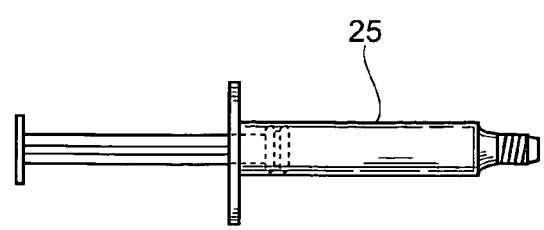
FIG. 5 is a side view of an air sample collection apparatus such as a syringe.

Referring now to FIGS. 3 and 4, a closed loop system is disclosed. In this system, the test tube 25 is evacuated of waste air in the peristaltic pump tubing 37 once peristaltic pump 20 engages, filling initially empty syringe 25 with waste air. Waste air is air in the peristaltic pump tubing 37 that is not air intended to be sampled or analyzed.

Figures 6, 7:
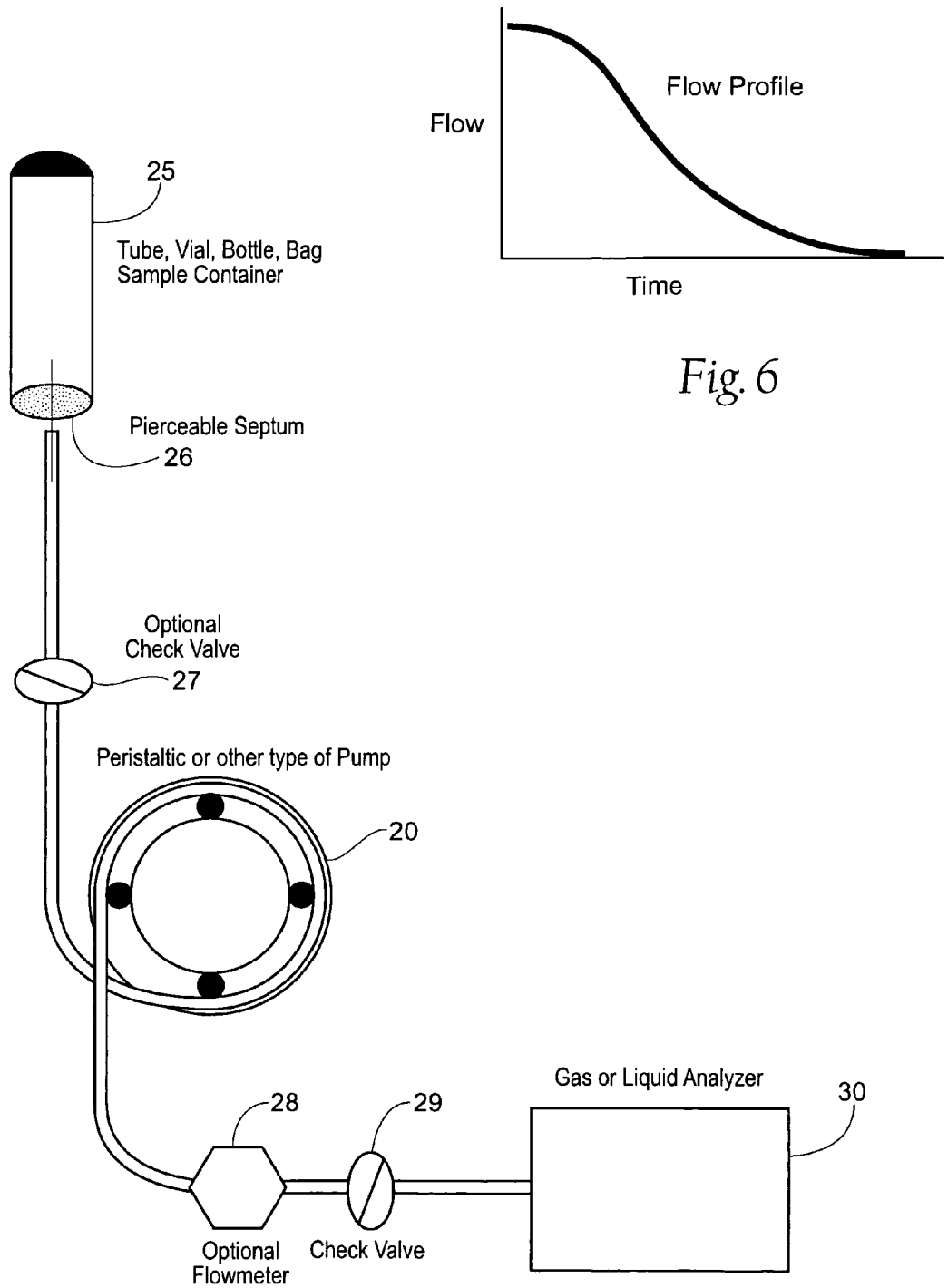
FIG. 6 is a flow profile.
FIG. 7 is a schematic drawing of a sample extraction apparatus and method for transferring the air sample to an analyzer.

Referring now to FIG. 7, a schematic drawing of a sample extraction apparatus and method for transferring the air sample to an analyzer is shown. An evacuated tube or container 25 is filled with a substance to be analyzed, and a pierceable septum 26 is provided to maintain the sample prior to extraction for further downstream testing. The septum 26 is pierced and the pump 20 extracts the sample to the analyzer 30. The pump 20 is started and runs for a period of time that matches the flow profile shown in FIG. 6, whereby the pump would stop at a time when the flow reaches zero or very close to zero. Alternatively, a flowmeter 28 would provide an electronic signal to control electronics to stop the pump 20 at zero or near zero flow condition. When the pump 20 stops, the operator would active the gas or liquated analyzer.

It is preferred that the sample extractor operates on timed runs based on a typical flow profile shown in FIG. 6, such as test tubes holding breath samples. A universal device could also monitor flow and control on/off with a microprocessor unit.

Figure 8:
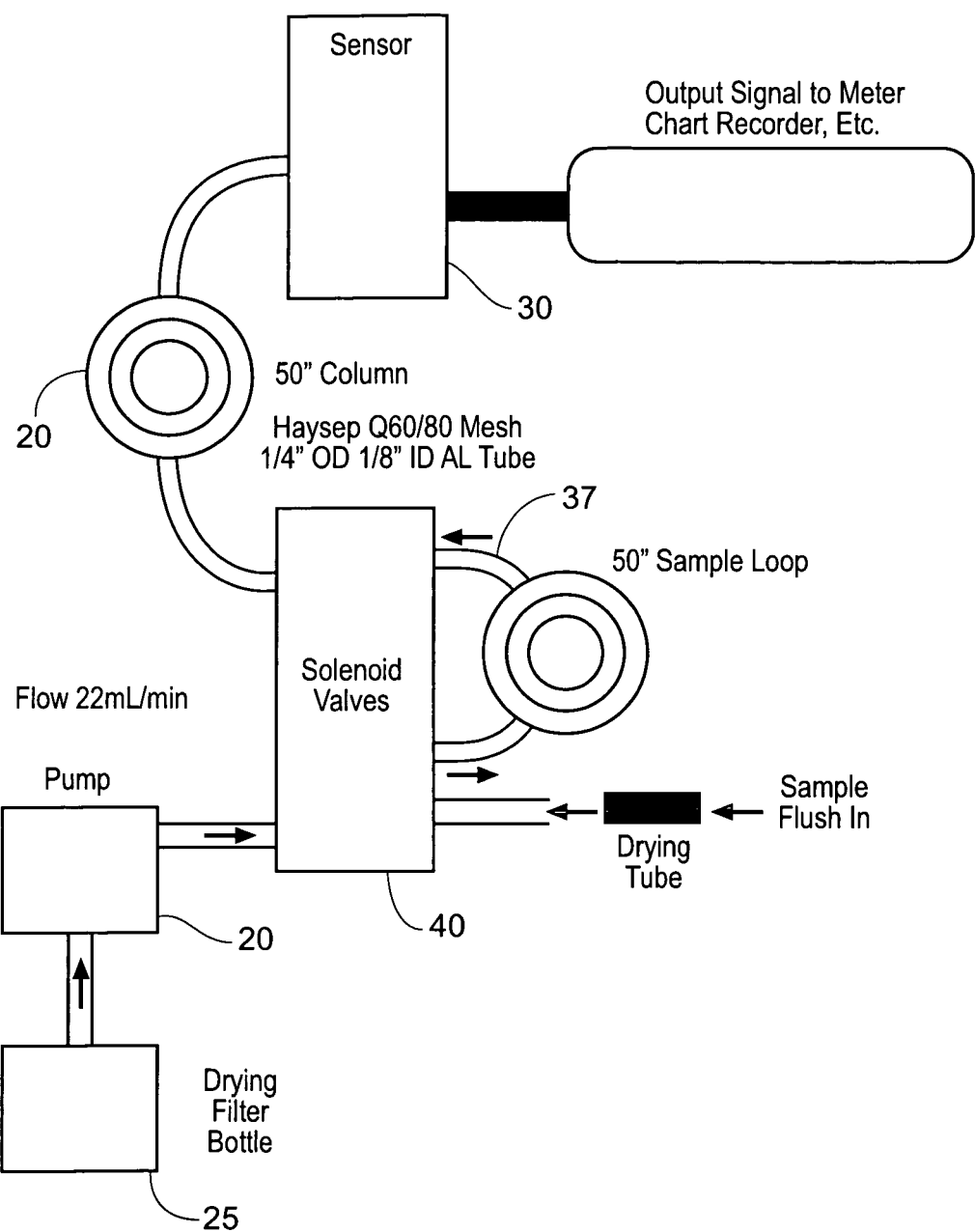
FIG. 8 is a schematic drawing of an alternate embodiment of a sample extraction apparatus and method for transferring the air sample to an analyzer.

Referring now to FIG. 8, a schematic drawing of an alternate embodiment of a sample extraction apparatus and method for transferring the air sample to an analyzer is shown. In this embodiment, drying filter bottle is evacuated by pump 20, and the air exist pump 20 into solenoid valves 40. The sample is coupled to a drying tub, which is also coupled to solenoid valves 40, and a sample loop is downstream. The exit of the sample loop, is coupled to a column as shown, with the preferable suppliers shown on FIG. 8. 60-80 mesh, matrix packed gas chromatography is preferred, with the sensor 30 provided coupled to output source. In this sense, a closed loop is provided.

Figure 9:
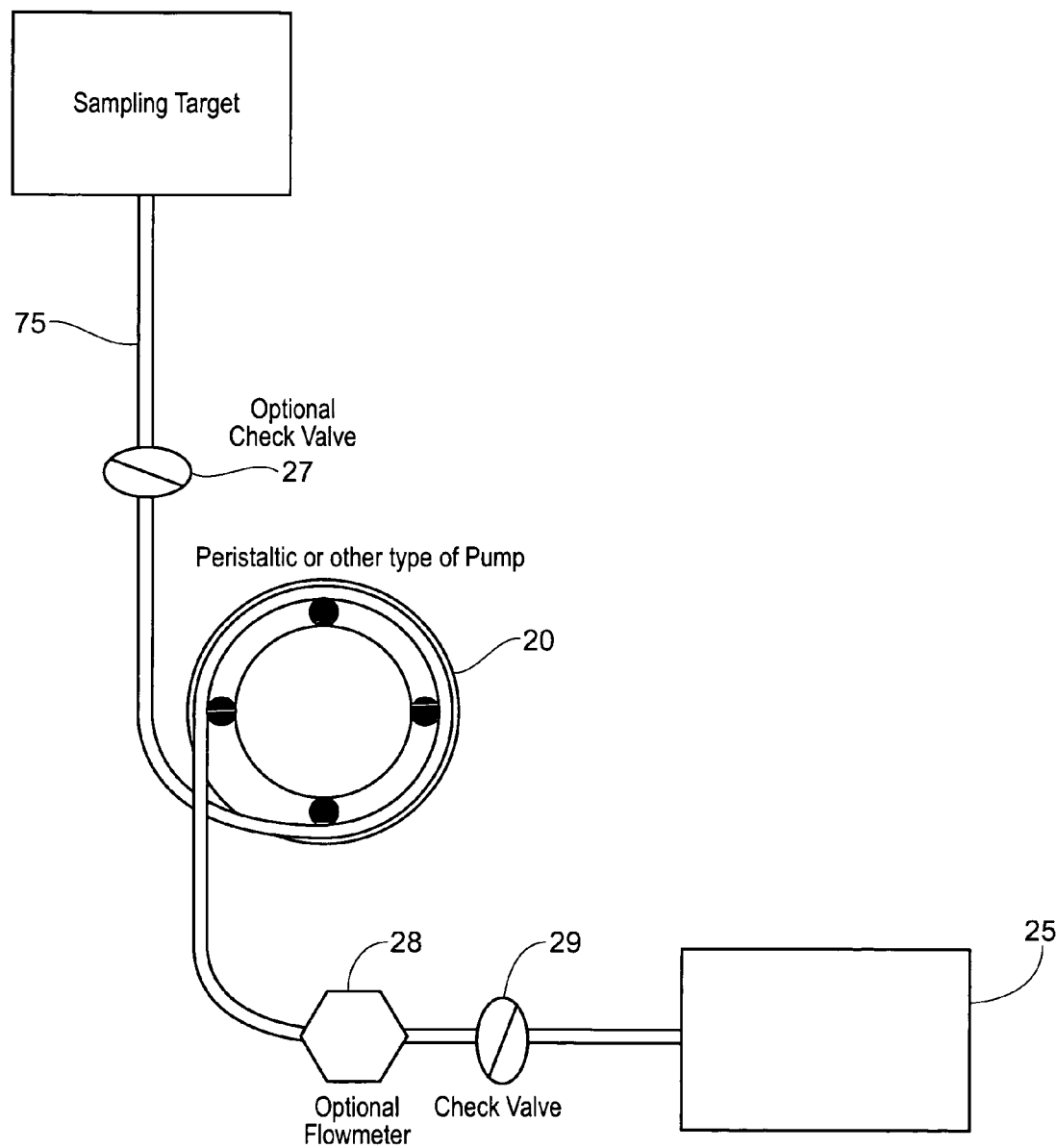
FIG. 9 is a schematic drawing of a alternate sample extraction apparatus and method for collecting an air sample into an analyzer.

FIG. 9 is a schematic drawing of an alternate sample extraction apparatus and method for collecting an air sample into an analyzer. In contrast to earlier referenced embodiments, in which removal of samples from evacuated spaces or filled sample containers (tubes, vials, bottles, or bags) is shown, the method and apparatus shown in FIG. 9 can be used to collect samples from their target area which can be an open environment, such as environmental or medical situations, sanitation situations, mining applications, or utilities. In such situations, monitoring ambient or moving air for particular gases or contaminants may be desirable.

Instead of using syringe to collect sample (FIG. 7), or a bag (FIG. 1), one can use a vacuum tube 75 exposed to the sampling target, which can be either at atmospheric or non-atmospheric pressure. This system uses a peristaltic pump 20 which draws a vacuum back on through the vacuum tube 75 extracts sample out and pushes the sample to either a container 25 (such as the container 25 used to initially store sample as shown in FIG. 7), or directly to a gas or liquid analyzer 30. This positive pumping method differs from prior art movement of air samples in that traditional water displacement techniques, in which water is introduced to the sample in order to evacuate the sample from the space now occupied by the water is used. Alternatively, nitrogen injection has been used and introduced into the sample to likewise evacuate the sample from the space it formerly occupied.

In one method of the present invention, the pump 20 can be programmable as is known in the art, in order to turn on and off and collect a predetermined volume of sample, or a operate for a predetermined amount of time. In this method, aggregate sampling can be accomplished by operating the pump 20 either continuously or at intervals until a predetermined volume is collected. The systems and methods of the present invention can be used to operate pumps 20 that are programmable or otherwise operated in a manner for turning on and off to collect aggregate samples. For instance, some sampling procedures require a predetermined volume for testing. Alternatively, concentrators are used to aggregate samples to measure for very small concentrations of sample analyte. In this manner, the programmable pump 20 can operate through flowmeter 28 and either volume or time calculations can be performed on the sample aggregation. Referring to the flow meter 28, this has been incorporated into the system so that a predetermined volume can be collected, or if less than the full volume of a container is withdrawn, concentration can be accurately determined.

Alternatively, pump 20 can be operated for a predetermined amount of time at a predetermined flow rate to result in a predetermined volume. This technique could be used to either fill a container for samples, or to send a predetermined volume of sample to the instrument for measurement (e.g., concentrators where material is adsorbed or absorbed into the concentrator). Alternatively, a predetermined amount of sample, or an aliquot can be transported positively into the analyzer 30. In a case where sample collection is required, a certain amount is pumped out over time into a sample collection bag (e.g., 10 ml every 60 minutes over 24 hours to result in a predetermined volume). This technique can be applied to any type of vessel or atmosphere that contains desired sample, and after passing through the pump 20, could result in either collection in collector 25 or analysis into analyzer 30. This technique, as opposed to displacing the sample with water or a benign gas (e.g., nitrogen) keeps the sample in its pure form, reducing the amount of contaminants introduced into the analysis.

If necessary or desirable, a chromatographic footprint can be created for ambient contaminants in the system, or pump 20 plus tube 75, and that footprint could be subtracted from the results of the analyzer 30.

A closed system is disclosed without contaminating connections or sample transfer techniques, and the present methods can be utilized to target atmospheric or non-atmospheric targets. A closed system is defined as a system not subject to the atmosphere between the situs of the target analyte and the gas or liquid analyzer.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method for sampling gas, the method comprising:
creating a closed system between a situs of a target analyte and a gas analyzer;
operating a peristaltic pump between said situs of a target analyte and said gas analyzer to transport the gas from the situs first to the peristaltic pump and next to at least one of said analyzer and a sample container;
operating said peristaltic pump to generate a variable flow rate decreasing non-linearly through time, and discontinuing said operation as said flow nears zero;
said situs comprising a vacuum container having a piercable septum, said vacuum container having subsequently been filled with an air sample for analyzing.

2. The method of claim 1, wherein the situs of a target analyte is at atmospheric pressure.

3. The method of claim 1, wherein the situs of a target analyte is at non-atmospheric pressure.

4. The method of claim 1, the method further comprising passing the gas through a flowmeter.

5. A method according to claim 1, the method further comprising operating said pump until flow reaches substantially zero.

6. A method of claim 1, the method further comprising transporting a predetermined volume of gas aliquot.

7. A method according to claim 1, the method further comprising operating the peristaltic pump between said sites of a target analyte and said gas analyzer to transport the gas from the situs first to the peristaltic pump and next to a solenoid valve, and next through a sample loop, next through a column, and next to at least one of an analyzer and a sample container.

8. A method according to claim 1, the method further comprising operating the peristaltic pump to draw said air sample for analyzing into said situs of said target analyte, and transporting said target analytic to said at least one of said analyzer and said sample container.

* * * * *